United States Patent

Nadal

[11] Patent Number: 5,984,903
[45] Date of Patent: Nov. 16, 1999

[54] CATHETER HAVING A VALVE WITH A BI-DIRECTIONAL AXIAL SLITS

[75] Inventor: Guy Nadal, Poitiers, France

[73] Assignee: B. Braun Celsa, France

[21] Appl. No.: 08/894,287

[22] PCT Filed: Dec. 11, 1996

[86] PCT No.: PCT/FR96/01983

§ 371 Date: Aug. 21, 1997

§ 102(e) Date: Aug. 21, 1997

[87] PCT Pub. No.: WO97/23255

PCT Pub. Date: Jul. 3, 1997

[30] Foreign Application Priority Data

Dec. 21, 1995 [FR] France .................... 95 15281

[51] Int. Cl.$^6$ ........................................ A61M 5/00
[52] U.S. Cl. ........................................ 604/256; 604/247
[58] Field of Search .................... 604/167, 169, 604/246, 247, 256, 264, 280

[56] References Cited

U.S. PATENT DOCUMENTS

| | | |
|---|---|---|
| 4,475,898 | 10/1984 | Brodner et al. ............ 604/247 X |
| 5,000,745 | 3/1991 | Guest et al. ............ 604/256 |
| 5,030,210 | 7/1991 | Alchas ............ 604/247 |
| 5,085,635 | 2/1992 | Cragg ............ 604/256 X |

FOREIGN PATENT DOCUMENTS 2707505  7/1993  France .................... 604/256

*Primary Examiner*—Wynn Wood Coggins
*Assistant Examiner*—A. T. Nguyen
*Attorney, Agent, or Firm*—Rothwell, Figg, Ernst & Kurz

[57] ABSTRACT

The catheter is a catheter for controlling the circulation of fluid through it, from or to a vessel in which the catheter is inserted. The catheter comprises a long tubular body that is open especially at its distal end (5), over which there is arranged a cap (5) having an essentially flat distal wall (7) in which there is formed at least one slit forming a valve (7).

The slit in the cap has a length that is greater than or equal to the inside diameter of the body of the catheter. The said slit preferably extends also into the side of the cap, and a tube is inserted into the distal portion of the catheter in order to support the sleeve during aspiration.

9 Claims, 1 Drawing Sheet

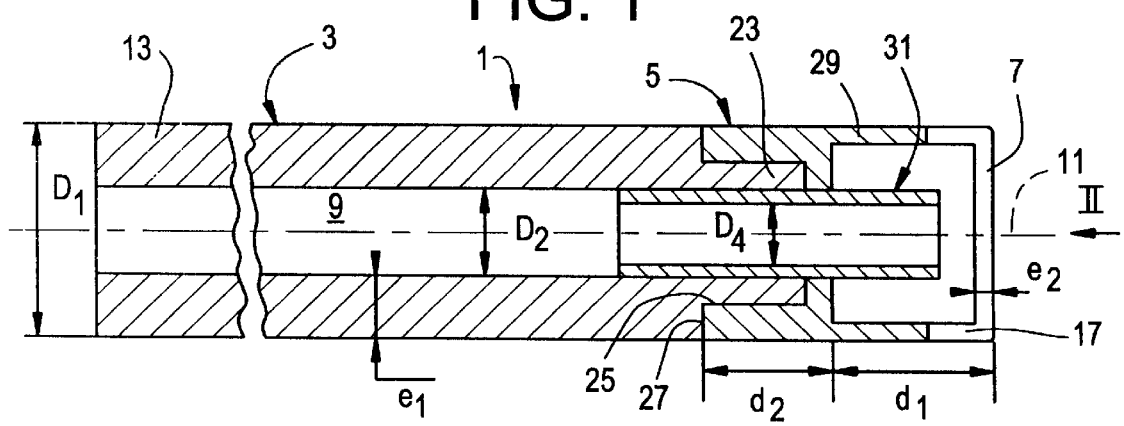
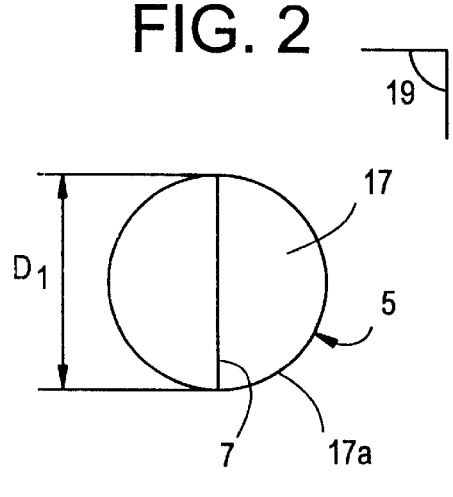
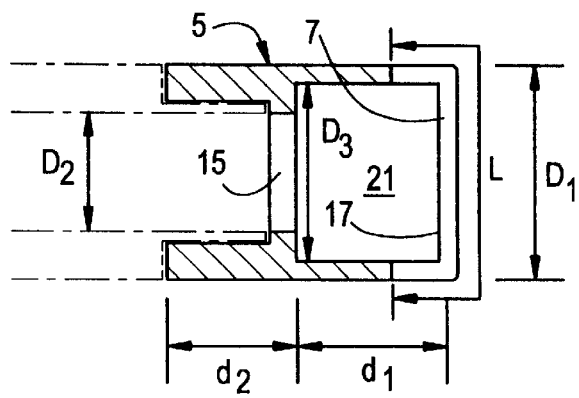
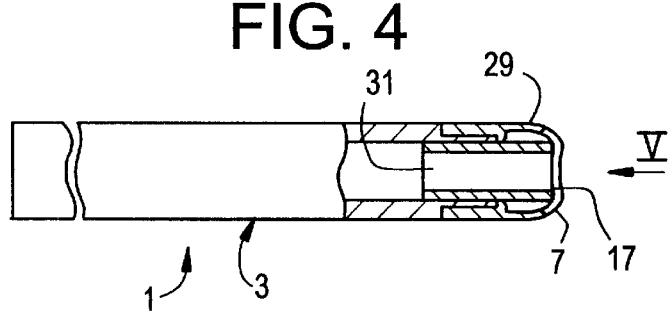
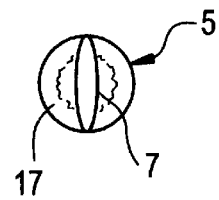
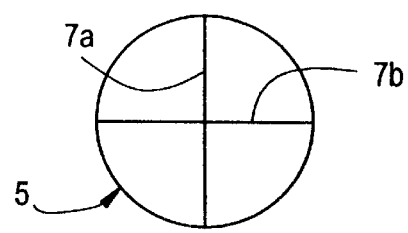

CATHETER HAVING A VALVE WITH A BI-DIRECTIONAL AXIAL SLITS

BACKGROUND OF THE INVENTION

1. Field of the Invention

The invention relates to a catheter comprising a valve for controlling fluid (especially liquid) at its distal end by which it is inserted into a duct of a human or animal body, in order to control the distribution of fluid from the catheter into said duct or the removal of fluid from the duct.

In particular, the catheter of the invention is a vascular catheter adapted to be inserted into a vessel in such a manner that its distal end is located therein, either in order to remove blood, for example, from the vessel or to inject a treatment product into the vessel.

2. Description of Background Art

Several intravenous therapies, including the administration of chemotherapeutic medicaments and hyper-feeding, require the use of such a vascular catheter that is suitable for remaining in the patient's body for an implantation period that may sometimes last several weeks.

Typically, such a catheter is implanted by the femoral or jugular route (then through the subclavian vein, towards the upper vena cava).

Of the existing vascular catheters, that of EP-A-328 332 (or U.S. Pat. No. 5,030,210) is known in particular.

As in the invention, it is a "two-way" catheter for controlling the circulation of fluid through it from, or to, a duct of a human or animal body in which the catheter is inserted.

That catheter has a principal axis and comprises:

a long tubular body extending along the principal axis and having an internal passage, an inside diameter, an outside diameter, and a distal end having an opening that communicates with the passage, a cap that is located over the open distal end of the body and is fixed to the body, the cap having an essentially flat distal wall facing the open distal end of the body, and at least one slit forming a valve that is formed through said flat distal wall of the cap, to communicate with the passage in the body of the catheter, the valve reacting to pressure differences on either side of it, for the circulation of fluid from, or to, the duct.

In the above-mentioned patent it is indicated that the catheter disclosed therein has been optimised for the circulation of liquid, within the context of intravascular implantation.

In particular, it is indicated therein that the problem of circulating liquid in both directions (from or to the catheter) has been taken into consideration; the proposed catheter is supposed to provide such bi-directional operation, in particular without causing the catheter to fold or collapse in on itself on aspiration.

The proposed solution also claims to provide the distal end of the catheter with a structure that is sufficiently thick that it will not fold or become blocked as a result of movements of the patient, muscular movements or an aspiration vacuum; moreover, the valve slit arranged in a relatively thin wall covering the open distal end of the catheter is said to permit a rapid reaction of the valve to differences in pressure.

The catheter of EP-A-328 332, or U.S. Pat. No. 5,030,210, has a catheter body preferably made of polyurethane and having a thickness of approximately from 0.25 to 0.75 mm. The cap has a wall thickness of preferably from 0.05 to 0.25 mm. Silicone rubber, polyvinyl chloride, polyethylene or polytetrafluoroethylene may also be used. A single slit forming a valve is provided, its length being approximately from 30 to 70% of the inside diameter of the catheter. The slit arranged in the distal end wall of the cap is flattened against the open distal end of the body of the catheter, in such a manner that there is no gap between the distal ends of the body and of the cap.

Within the context of the present invention it is maintained that a further real improvement in operation, especially on aspiration, can be achieved and that a further improvement can likewise be obtained in the manner in which the problem of the wall surrounding the valve slit collapsing in on itself is resolved, in particular within the context of vascular catheters provided for injecting a treatment liquid into a vessel in one direction and, in the opposite direction, for allowing the removal of, especially, blood or a body fluid.

For bi-directional operation to be possible it is essential to ensure that the valve will open correctly (in one direction or the other) for a predetermined pressure difference and that it will remain closed, by its lips being in contact with each other, if that pressure difference is not achieved, without damaging the integrity of the catheter, its necessary flexibility associated with mechanical strength, and the resistance that must be provided in view of the consequences of unexpected movements of the catheter inside the patient's body.

In accordance with the solution of the invention, the catheter described above in connection with EP-A-328 332 has a cap, the slit(s) of which has (have) a length that is at least equal to the inside diameter of the body of the catheter. Another characteristic that is also used to solve in particular the problem of the walls surrounding the slit forming the valve collapsing in on themselves, especially on aspiration, is that the flat distal wall of the cap is located at a distance from the distal end of the body of the catheter.

Especially with such a characteristic, and if the distal wall of the cap is in the form of a full circular disc that is split, it will be possible to lengthen the slit(s) in such a manner that the length of the slit(s) is greater than the outside diameter of that wall. In fact, it has been found that very good operation is obtained if the length of the slits(s) (especially two slits in a cross extending in two perpendicular directions) is (per slit) from 1.5 to 2.5 times the inside diameter of the catheter, that is to say in fact much greater than the outside diameter of the cap, since that outside diameter is only several tenths of a millimeter (indeed possibly several millimeters) larger than the inside diameter of the body of the catheter.

A further problem to be solved by the invention concerns the flow rate of fluid that is to be able to pass through the valve. In fact, it has been found that existing "two-way" catheters only allow flow rates that are too weak to satisfy the users' requirements. Therefore, the invention solved that problem, by requiring, moreover, that the flow rate through the valve be comparable to that which would exist for the same catheter, but without a cap, and for the same pressure. It is likewise to be noted that while designing the present catheter it was found that the problem to be solved is associated both with the manner in which the valve is formed and with certain characteristics of the cap.

SUMMARY OF THE INVENTION

The solution provided by the invention, in connection with the above, is:

that the cap has a substantially cylindrical side wall, that the cap has an inside diameter that is comparable to, and preferably larger than, the inside diameter of the body of the catheter, and that the slit(s) forming the valve extend(s) both over the distal wall of the cap and into its cylindrical side wall.

It is to be noted that the expression "comparable" is to be interpreted as meaning that the inside diameter of the cap may be substantially equal (to 2 or 3 tenths of a millimeter) to the inside diameter of the body of the catheter.

Another way of presenting that solution is to produce the catheter of the invention in such a manner that:

the valve comprises at least two slits arranged in a cross, each slit having a length of approximately from 3 mm to 4.5 mm, and the cap has an outside diameter of approximately from 2.2 mm to 2.8 mm and an inside diameter that is more than approximately 0.3 mm larger than the inside diameter of the body of the catheter. In both cases, the distal wall of the cap, in which the valve is formed, will of course extend at a distance from the distal end of the body of the catheter.

According to another characteristic of the invention, and again in order to solve the problems already mentioned, the catheter will be strengthened internally towards its distal end in order to provide support for a wall of the cap when the valve is operating to circulate liquid on aspiration.

The internal strengthening will advantageously be provided by means of a tube inserted into the internal passage in the body of the catheter.

If, as is preferred, the distal wall of the cap, in which the valve is formed, extends at a distance from the open distal end of the body of the catheter, the internal strengthening piece will likewise extend beyond that end, inside the chamber so formed in the cap.

According to a further characteristic, if the strengthening piece is a tube, the tube will have an inside diameter that is advantageously smaller than the inside diameter of the body of the catheter, and the cap will have an inside diameter that is larger than the outside diameter of the said tube.

In that manner it will be possible to obtain a "Venturi" effect, which is favourable to achieving the desired flow rate of fluid through the catheter, while creating conditions in which the cap is supported, which is favourable to aspiration.

As a construction characteristic of the catheter of the invention, it may also be noted that the latter are very important according to the type of implantation, those characteristics being described in the description which follows, which refers to the attached drawings in which:

BRIEF DESCRIPTION OF THE DRAWING

FIG. 1 is a longitudinal section of a catheter according to the invention,

FIG. 2 is a front view in the direction of the arrow II in FIG. 1 (with the section of FIG. 1 being completed by symmetry), FIG. 3 is a view of the cap alone, in section as in FIG. 1, FIG. 4 shows diagrammatically, in longitudinal section, the deformation that the cap may experience on aspiration, FIG. 5 is a front view (completed by symmetry) according to arrow V in FIG. 4, and FIG. 6, like FIGS. 2 and 5, is a front view, but of a catheter having a double slit in a cross forming the distal valve.

DETAILED DESCRIPTION OF THE PREFERRED EMBODIMENTS

In FIG. 1, first of all, the catheter of the invention, which is designated as a whole by 1, comprises a catheter body 3 associated with a cap 5 in the wall of which there is formed a bi-directional valve having at least one slit 7.

The body 3 is a flexible catheter tube having an open proximal end 13 and a distal end that is likewise open, 23.

Inside, the catheter tube 3 has a passage 9 extending along the principal axis 11 of the catheter, between the proximal and distal ends, the passage ending in openings, such as that numbered 15 at the distal end (see FIG. 3).

The cap 5 is fitted onto that opening 15.

Like the body 3, the cap 5 is here essentially in the form of a tubular cylinder having a circular cross-section. Unlike the body, however, it has a free wall at the frontal, or distal, end 17 (see FIG. 2). That distal wall is essentially flat and has a circular peripheral edge that is advantageously rounded atraumatically, 17a.

The plane 19 in which the distal wall 17 extends, at least essentially, is preferably substantially perpendicular to the principal axis 11 of the body and of the catheter as a whole, thus avoiding one operating direction of the valve being favoured over the other.

The valve 7 is formed through the entire thickness of the thin distal wall, and is substantially centred therein. In FIGS. 1 to 5, there is a single slit. However, several slits, such as two slits in a cross as in FIG. 6, may be preferred.

For optimum operation, the valve 7 having (a) slit(s) will be located at an axial distance d1 from the distal end 23 of the body 3. The cap 5 will thus have a kind of cylindrical internal chamber 21.

For fixing of the cap 5, the cap engages a surface 25 of the catheter tube that extends over an axial distance d2, starting from the end 23, in the direction towards the end 13.

Accordingly, in the version of FIG. 1, the cap may be regarded as comprising two portions, one for fixing to the tube 3 (and having a length d2) and the other, having a length d1, being intended for the optimum bi-directional operation of the valve 7.

Since the outside diameter of the catheter is in many cases critical, in view of the implantation conditions in vessels of small diameters, it is preferable for the body 3 and the cap 5 to have substantially the same outside diameter D1.

To that end, the thickness $e_1$ of the body 3 is reduced at the surface 25, following a shoulder 27, it being possible to fix the cap with regard to the surface 25 by adhesive bonding, or by any other method of intimate bonding.

For the valve 7 to operate correctly, the thickness $e_2$ of the cylindrical side wall 29 located beyond the distal end 23 will advantageously be less than the thickness of the wall of the fixing zone 25 and, of course, less than the thickness $e_1$ of the catheter tube. The desired balance between sufficient structural resistance of the distal portion of the catheter and the required flexibility in the area of the valve will thus be favoured.

In connection therewith it is, moreover, important within the scope of the invention that the slit(s) 7 has (have) a length L (see FIG. 3) that is greater than or equal to the inside diameter of the tube 3 at least at its distal end, that diameter being in the case in point constant over the entire length of the tube and corresponding to the inside diameter, D2, of the passage 9.

In practice, it has even been found that optimisation of bi-directional operation could be obtained if the length of the valve having (a) slit(s) was at least equal to the outside diameter D1, even, advantageously, greater than that diameter. Furthermore, it is for that reason that it will be seen, especially in FIGS. 1 and 3, that the slit 7 extends beyond the wall 17, into a portion of the cylindrical side wall 29.

A slit length of (per slit) from 1.5 to 2.5 times the diameter D2 is advised, especially if the hardness of the cap 5 is approximately from 45 to 55 Shores A, the common outside diameter D1 (or at least the outside diameter of the cap) is of the order of from 2.2 mm to 2.8 mm (preferably approximately 2.5 mm), the diameter D2 is of the order of from 1.1 to 1.4 mm, the inside diameter D3 of the cap is approximately from 1.8 to 2 mm and the valve is composed of two perpendicular slits in a cross (see FIG. 6), each slit having a length L of approximately from 3 mm to 4.5 mm, preferably approximately from 3.8 mm to 4 mm. In such an embodiment, the thickness $e_2$ of the walls 17 and 29 will advantageously be of the order of 0.3 mm, the thickness $e_1$ of the order of 0.5 mm, and the hardness of the body 3 of the order of from 60 to 70 Shores A.

Both the body and the cap may be made of silicone rubber, suitable for vascular implantation.

According to another very advantageous characteristic of the invention it will be noted, furthermore, in particular in FIG. 1, that the distal end of the body 3 has been "strengthened" internally by means of a structure 31 that is to provide support for the cap when the valve 7 is to operate for aspiration.

The structure 31 shown is a tube inserted into the passage 9, from the distal end 23.

Especially if the valve 7 is at a distance from the end 23, the strengthening piece 31 will preferably also extend towards the slit, inside the chamber 21 in the cap.

If the strengthening piece is a tube, it may be made of silicone or polyurethane and have a length of several millimeters.

Its inside diameter D4 will preferably be smaller than the diameter D2. As regards its outside diameter, it will be substantially equal to D2. A "Venturi" effect will thus be created between the passage 9 and the valve 7 (or the chamber 21), which is favourable to the circulation of the liquid with the desired flow rate.

When a treatment product is to be ejected from the catheter after circulating in the passage 9, the valve 7 will operate for ejection by the lips of the slit opening and being deformed slightly outwards, substantially in the manner of a mouth that opens with the lips moving forwards.

On aspiration, if an excess of pressure is acting on the outside of the slit, for the purpose of circulating, for example, blood to the passage 9, the catheter will then assume substantially the shape shown in FIG. 4, with the lips of the valve being slightly apart as in FIG. 5.

In FIG. 4 it will be noted in particular that, during such an aspirating operation, the walls 17 and/or 29 of the cap are deformed inwards until they come to rest on the tube 31; excessive collapsing of the cap, with the risk of the valve being prevented from operating correctly and the slit even being closed, is thus avoided.

FIG. 6 shows, as already indicated, that the valve may comprise a multiple slit that has, for example, two parts split in a cross, 7a, 7b. If desired, more than four sectors may even be provided. Of course, the (each) slit is produced as a local cut through the entire thickness of the wall in question, without any material being removed.

What is claimed is:

1. A catheter for controlling the circulation of fluid therethrough, from or to a duct of a human or animal body in which the catheter is inserted, the catheter comprising:

a tubular body having a principal axis and having an outside diameter, an internal passage of an inside diameter, and a distal end having an opening that communicates with the passage;

a cap that is affixed to the distal end of the body of the catheter, the cap having an essentially flat distal wall facing the open distal end of the body; and a slit forming a valve through the flat distal wall of the cap, to communicate with the passage in the body of the catheter, the valve reacting to pressure differences on either side thereof, for the circulation of the fluid from or to the duct, the slit having a length that is greater than or equal to the inside diameter of the body of the catheter;

wherein the flat distal wall of the cap is spaced from the distal end of the catheter body by a predetermined distance and wherein a cavity is formed between the flat distal wall of the cap and the distal end of the catheter body, said catheter further comprising an internal strengthening tube disposed coaxially within the internal passage of the catheter body and extending beyond the distal end thereof and into the cavity.

2. Catheter according to claim 1, wherein the fluid to be circulated through the catheter is a liquid and the catheter is a vascular catheter adapted to be inserted into a vessel.

3. Catheter according to claim 1, wherein the length of the at least one slit is from 1.5 to 2.5 times the inside diameter of the body of the catheter.

4. Catheter according to claim 1, wherein:

the cap has a substantially cylindrical side wall;

the cap has an inside diameter that is substantially equal to or larger than the inside diameter of the body of the catheter; and the slit extends both over the distal wall of the cap and into the cylindrical side wall thereof.

5. Catheter according to claim 1, wherein the tube has an inside diameter that is smaller than the inside diameter of the catheter body, and the cap has an inside diameter that is larger than the outside diameter of the tube.

6. Catheter according to claim 1, wherein the valve comprises two intersecting slits formed through the flat distal wall of the cap.

7. Catheter for controlling the circulation of fluid therethrough, from or to a duct of a human or animal body in which the catheter is inserted, the catheter comprising:

a tubular body having a principal axis and having an outside diameter, an internal passage of an inside diameter, and a distal end having an opening that communicates with the passage;

a cap that is affixed to the distal end of the body of the catheter, the cap having an essentially flat distal wall facing the open distal end of the body; and a slit forming a valve through the flat distal wall of the cap, to communicate with the passage in the body of the catheter, the valve reacting to pressure differences on either side thereof, for the circulation of the fluid from or to the duct, the slit having a length that is greater than the outside diameter of the flat distal wall of the cap;

wherein the flat distal wall of the cap is spaced from the distal end of the catheter body by a predetermined distance.

8. Catheter for controlling the circulation of fluid therethrough, from or to a duct of a human or animal body in which the catheter is inserted, the catheter comprising:

a tubular body having a principal axis and having an outside diameter, an internal passage of an inside diameter, and a distal end having an opening that communicates with the passage;

a cap that is affixed to the distal end of the body of the catheter, the cap having an essentially flat distal wall facing the open distal end of the body; and a slit forming a valve through the flat distal wall of the cap, to communicate with the passage in the body of the catheter, the valve reacting to pressure differences on either side thereof, for the circulation of the fluid from or to the duct, the slit having a length that is greater than or equal to the inside diameter of the body of the catheter;

wherein the flat distal wall of the cap is spaced from the distal end of the catheter body by a predetermined distance; and wherein the valve comprises at least two slits arranged in a cross formation, each slit having a length of approximately from 3 mm to 4.5 mm;

wherein the cap has a hardness of approximately 45 to 55 Shores A, an outside diameter of approximately from 2.2 mm to 2.8 mm, and an inside diameter that is more than approximately 0.3 mm larger than the inside diameter of the body of the catheter.

9. Catheter for controlling the circulation of fluid therethrough, from or to a duct of a human or animal body in which the catheter is inserted, the catheter comprising:

a tubular body having a principal axis and having an outside diameter, an internal passage of an inside diameter, and a distal end having an opening that communicates with the passage, a cap that is affixed to the distal end of the body of the catheter, the cap having an essentially flat distal wall facing the open distal end of the body, and a slit forming a valve through the flat distal wall of the cap, to communicate with the passage in the body of the catheter, the valve reacting to pressure differences on either side thereof, for the circulation of the fluid from or to the duct, the slit having a length that is greater than or equal to the inside diameter of the body of the catheter, wherein the flat distal wall of the cap is spaced from the distal end of the catheter body by a predetermined distance and a cavity is formed between the flat distal wall of the cap and the distal end of the catheter body, the catheter further comprising an internal strengthening tube disposed coaxially within the internal passage of the catheter body and extending beyond the distal end thereof and into the cavity, to provide support for a substantially cylindrical wall of the cap when the valve is operating to circulate fluid from the duct to the passage of the body.

* * * * *